United States Patent
Stelzer et al.

(10) Patent No.: US 6,500,986 B1
(45) Date of Patent: *Dec. 31, 2002

(54) PROCESS FOR PREPARING RACEMIC AMINO DERIVATIVES

(75) Inventors: Uwe Stelzer, Burscheid (DE); Johannes Rudolf Jansen, Monheim (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1060 days.

(21) Appl. No.: 08/693,929

(22) Filed: Aug. 5, 1996

(30) Foreign Application Priority Data

Aug. 9, 1995 (DE) ......................... 195 29 293

(51) Int. Cl.⁷ ............................. C07C 209/00
(52) U.S. Cl. ................................... 564/302
(58) Field of Search ........................ 564/302

(56) References Cited

U.S. PATENT DOCUMENTS

| | | | | |
|---|---|---|---|---|
| 3,969,397 A | * | 7/1976 | Kaiser et al. | 260/501.11 |
| 5,047,585 A | * | 9/1991 | Boesten et al. | 564/124 |
| 5,183,939 A | | 2/1993 | Jansen et al. | |
| 5,376,671 A | * | 12/1994 | Muller-Gliemann et al. | 514/399 |

FOREIGN PATENT DOCUMENTS

| | | | |
|---|---|---|---|
| DE | 40 38 356 A1 | | 6/1992 |
| DE | 43 32 738 A1 | | 3/1995 |
| DE | 43 32 738 | * | 3/1995 |
| EP | 0 399 589 | | 11/1990 |
| FR | 2 027 209 | | 9/1970 |
| FR | 2 387 929 | | 11/1978 |

OTHER PUBLICATIONS

Reetz et al., "Highly efficient lipase–catalyzed kinetic resolution of chiral amines". Chimia, vol. 48, p. 570, 1997, 1994.*

J. March, "Advanced Organic Chemistry", second edition, p. 353, 1977.*

E. Dominguez et al, Tetrahedron. vol. 44, No. 1, pp. 203–208 (1988).

Manfred T. Reetz et al; Highly Efficient Lipase–Catalyzed Kinetic Resolution of Chiral Amines; Chimia 48 (1994) 570.

* cited by examiner

*Primary Examiner*—Barbara P. Badio
(74) *Attorney, Agent, or Firm*—Norris McLaughlin & Marcus

(57) ABSTRACT

Racemic amino derivatives of the formula

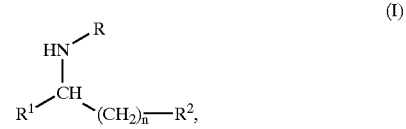

are prepared by a new process which comprises reacting an optically active amide of the formula

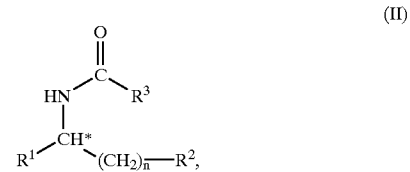

in which with a strong base, optionally in the presence of an organic diluent and, if desired, reacting the resulting racemic amide.

either a) with water in the presence of a base or an acid and optionally in the presence of an organic diluent, or b) if the compound of the formula (I) is an amide in which $R^3$ is hydrogen, with an alkali metal hydroxide or an alkaline earth metal hydroxide.

13 Claims, No Drawings

PROCESS FOR PREPARING RACEMIC AMINO DERIVATIVES

The present invention relates to a new process for preparing racemic amino derivatives by racemization of optically active amides.

Already known is the preparation of optically active amides by enantioselectively acylating racemic amines and separating the resulting mixture of optically active amine and optically active amide (=acylated amine) (cf. DE-A 43 32 738, Chimia 48, 570 (1994)). Furthermore, it is already known that optically active amides can be obtained by enantioselective hydrolysis of racemic amides and subsequent separation of the resulting mixture of optically active amide and optically active amine (cf. EP-A 0 399 589). In order to make these processes for resolution of racemates economical, the undesired enantiomer in each case has to be racemized again and returned to the circuit. If the component which is not required is an optically active amine, the racemization can be carried out by treatment with alkoxides in the presence of dimethyl sulphoxide (cf. DE-A 40 38 356). However, if the undesired isomer is an amide, a disadvantage of the work-up is that a saponification of the optically active amide is first required and the racemization of the optically active amine formed can only be carried out in a further step.

It has now been found that racemic amino derivatives of the formula

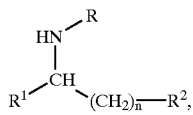
(I)

in which
n represents the numbers 0, 1 or 2,
$R^1$ represents unsubstituted or substituted alkyl, unsubstituted or substituted cycloalkyl, unsubstituted or substituted cycloalkenyl, unsubstituted or substituted aryl or unsubstituted or substituted heterocyclyl,
$R^2$ represents unsubstituted or substituted alkyl, unsubstituted or substituted cycloalkyl, unsubstituted or substituted cycloalkenyl, unsubstituted or substituted aryl or unsubstituted or substituted heterocyclyl, but with $R^1$ and $R^2$—$(CH_2)_n$— not being identical, and
R represents hydrogen or —CO—$R^3$, where
$R^3$ represents hydrogen, amino, unsubstituted or substituted alkyl or unsubstituted or substituted alkoxy, with the carbon chain being able, in the case of those radicals containing more than one carbon atom, to be interrupted by heteroatoms or hetero groups, or
$R^3$ represents unsubstituted or substituted cycloalkyl, unsubstituted or substituted cycloalkenyl, unsubstituted or substituted aryl or unsubstituted or substituted heterocyclyl,
are obtained when optically active amides of the formula

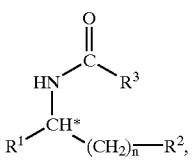
(II)

in which
$R^1, R^2, R^3$ and n are as defined above,
are reacted with strong bases, optionally in the presence of an organic diluent and, if desired, the resulting racemic amides of the formula

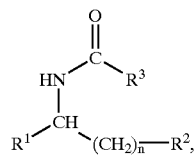
(Ia)

in which
$R^1, R^2, R^3$ and n are as defined above,
are reacted either
a) with water in the presence of a base or an acid and optionally in the presence of an organic diluent,
or
b) if the compounds of the formula (Ia) are amides in which $R^3$ is hydrogen, with alkali metal hydroxide or alkaline earth metal hydroxide.

It must be regarded as extremely surprising that racemic amides and amines can be prepared by the process of the invention, since it was not previously known from the prior art that racemization of optically active amides is possible without prior saponification.

The process of the invention has a series of advantages. Thus, it makes possible the preparation of racemic amides or amines from the respective undesired enantiomers in high yield. It is also advantageous that the optically active amides required as starting materials can be obtained in a simple manner and that the acyl radical can be varied within a wide range. Finally, the reaction procedure and the isolation of the desired substances also present no difficulties at all.

Alkyl represents, in the present case, unless otherwise defined, saturated aliphatic hydrocarbon radicals which can be straight-chain or branched.

Cycloalkyl represents, in the present case, unless otherwise defined, saturated, carbocyclic radicals which may optionally, together with further condensed-on or bridged rings, form a bicyclic or polycyclic ring system.

Cycloalkenyl represents, in the present case, unless otherwise defined, unsaturated, carbocyclic radicals which may optionally, together with further condensed-on or bridged rings, form a bicyclic or polycyclic ring system.

Aryl represents, in the present case, unless otherwise defined, aromatic, monocyclic, bicyclic or polycyclic hydrocarbon radicals such as phenyl, naphthyl, anthryl, phenanthryl, preferably phenyl or naphthyl, in particular phenyl.

Heterocyclyl represents, in the present case, unless otherwise defined, saturated or unsaturated, cyclic radicals in which at least one ring atom is a heteroatom, i.e. an atom different from carbon. If the ring contains a plurality of heteroatoms, these can be identical or different. Heteroatoms are preferably oxygen, nitrogen or sulphur. Optionally, the cyclic radicals together with further carbocyclic or heterocyclic, condensed-on or bridged rings, form a bicyclic or polycyclic ring system. Preference is given to monocyclic or bicyclic ring systems, in particular monocyclic or bicyclic ring systems having aromatic character.

In the definitions, the saturated or unsaturated carbon chains such as alkyl, alkanediyl, alkenyl or alkinyl, including those linked to groups bonded by heteroatoms, i.e. groups such as alkoxy, alkylthio or alkylamino are in each case straight-chain or branched.

Halogen represents, in the present case, unless otherwise defined, fluorine, chlorine, bromine or iodine, preferably fluorine, chlorine or bromine, in particular fluorine or chlorine.

If (S)-N-[1-(4-chlorophenyl)-ethyl]-acetamide is used as starting material and potassium hydroxide as strong base, then the course of the first stage of the process of the invention can be depicted by the following reaction scheme:

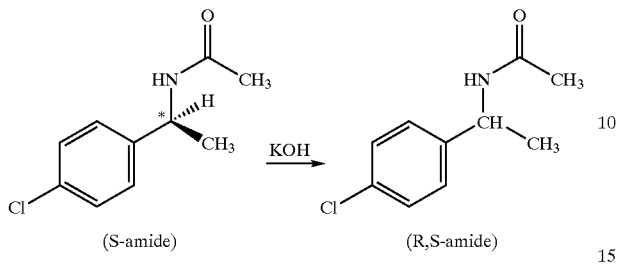

(S-amide) → (R,S-amide)

If racemic N-[1-(4-chlorophenyl)-ethyl]-acetamide is used as starting component and aqueous hydrochloric acid as reaction component, then the course of the second stage of the process of the invention can be depicted by the following reaction scheme:

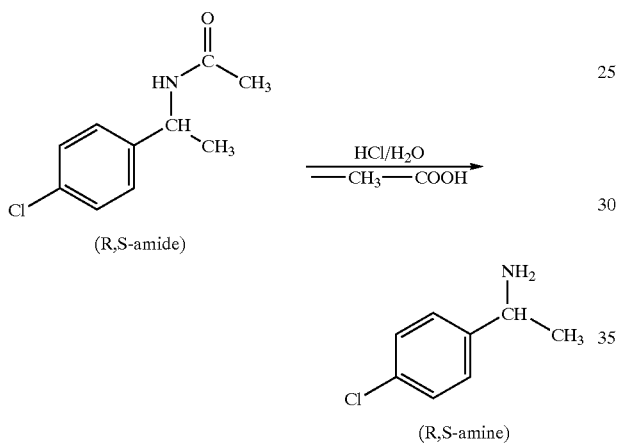

(R,S-amide) → (R,S-amine)

The optically active amides required as starting materials for carrying out the process of the invention are generally defined by the formula (II). In this formula, the asymmetrically-substituted carbon atom is denoted by (*). In other formulae for optically active compounds, centres of chirality are also each marked in the same manner.

n also preferably represents the numbers 0, 1 or 2.

$R^1$ preferably represents straight-chain or branched alkyl having from 1 to 8 carbon atoms, with the alkyl radicals being able to be monosubstituted or polysubstituted, identically or differently, by halogen, amino, hydroxy, formyl, carboxy, carbamoyl, straight-chain or branched alkoxy or straight-chain or branched alkylthio each having from 1 to 6 carbon atoms;

and/or by straight-chain or branched halogenoalkoxy or straight-chain or branched halogenoalkylthio each having from 1 to 6 carbon atoms and from 1 to 13 identical or different halogen atoms;

and/or by alkylamino, dialkylamino, alkylcarbonyl, alkylcarbonyloxy, alkoxycarbonyl, alkylsulphonyloxy, hydroximinoalkyl or alkoximinoalkyl which may each be straight-chain or branched and each have from 1 to 6 carbon atoms in the individual alkyl parts;

or by doubly linked alkylene having from 1 to 6 carbon atoms, or by doubly linked dioxyalkylene having from 1 to 4 carbon atoms, with the two latter radicals themselves being able to be monosubstituted or polysubstituted, identically or differently, by halogen, straight-chain or branched alkyl having from 1 to 4 carbon atoms and/or straight-chain or branched halogenoalkyl having from 1 to 4 carbon atoms and from 1 to 9 identical or different halogen atoms, or $R^1$ preferably represents cycloalkyl having from 3 to 7 carbon atoms, with these radicals being able to be monosubstituted to tetrasubstituted, identically or differently, by halogen and/or alkyl having from 1 to 4 carbon atoms, or represents cycloalkenyl having from 3 to 7 carbon atoms, with these radicals being able to be monosubstituted to tetrasubstituted, identically or differently, by halogen and/or alkyl having from 1 to 4 carbon atoms, or represents saturated or unsaturated heterocyclyl having from 3 to 7 ring atoms, of which in each case from 1 to 3 are identical or different hetero-atoms such as oxygen, nitrogen or sulphur, with the radicals being able to be monosubstituted to trisubstituted, identically or differently, by halogen, alkyl having from 1 to 4 carbon atoms, alkoxy having from 1 to 4 carbon atoms and/or halogenoalkyl having from 1 to 4 carbon atoms and from 1 to 5 identical or different halogen atoms, or represents aryl having from 6 to 10 carbon atoms, with each of these radicals being able to be monosubstituted to pentasubstituted, identically or differently, by halogen, straight-chain or branched alkyl having from 1 to 4 carbon atoms, straight-chain or branched halogenoalkyl having from 1 to 4 carbon atoms and from 1 to 9 identical or different halogen atoms, straight-chain or branched alkoxy or alkylthio having from 1 to 4 carbon atoms, straight-chain or branched halogenoalkoxy or halogenoalkylthio having from 1 to 4 carbon atoms and from 1 to 9 identical or different halogen atoms, phenyl, phenoxy, phenylthio, benzyloxy, benzylthio or phenylethyloxy, or by doubly linked alkylene having 3 or 4 carbon atoms or by doubly linked dioxyalkylene having 1 or 2 carbon atoms, with the two latter radicals themselves being able to be monosubstituted or polysubstituted, identically or differently, by halogen, straight-chain or branched alkyl having from 1 to 4 carbon atoms and/or straight-chain or branched halo-genoalkyl having from 1 to 4 carbon atoms and from 1 to 9 identical or different halogen atoms.

$R^2$ preferably represents straight-chain or branched alkyl having from 1 to 8 carbon atoms or $R^2$ preferably represents cycloalkyl having from 3 to 7 carbon atoms, with these radicals being able to be monosubstituted to tetrasubstituted, identically or differently, by halogen and/or alkyl having from 1 to 4 carbon atoms, or represents cycloalkenyl having from 3 to 7 carbon atoms, with these radicals being able to be monosubstituted to tetrasubstituted, identically or differently, by halogen and/or alkyl having from 1 to 4 carbon atoms, or represents saturated or unsaturated heterocyclyl having from 3 to 7 ring atoms of which in each case from 1 to 3 are identical or different hetero-atoms such as oxygen, nitrogen or sulphur, with the radicals being able to be monosubstituted to trisubstituted, identically or differently, by halogen, alkyl having from 1 to 4 carbon atoms, alkoxy having from 1 to 4 carbon atoms and/or halogenoalkyl having from 1 to 4 carbon atoms and from 1 to 5 identical or different halogen atoms, or represents aryl having from 6 to 10 carbon atoms, with each of these radicals being able to be monosubstituted to pentasubstituted, identically or differently, by halogen, nitro, amino, hydroxy, formyl, carboxy, carbamoyl, thiocarbamoyl; alkyl, alkoxy, alkylthio, alkylsulphinyl, or alkylsulphonyl which may each be straight-chain or branched and each have from 1 to 6 carbon atoms; straight-chain or branched alkenyl or straight-chain or branched alkenyloxy each having from 2 to 6 carbon atoms; halogenoalkyl, halogenoalkoxy, halogenoalkylthio, halogenoalkylsulphinyl or halogenoalkylsulphonyl which may each be straight-chain or branched and each have from 1 to 6 carbon atoms and from 1 to 13 identical or different halogen atoms;

straight-chain or branched halogenoalkenyl or straight-chain or branched halogenoalkenyloxy each having from 2 to 6 carbon atoms and from 1 to 13 identical or different halogen atoms; alkylamino, dialkylamino, alkylcarbonyl, alkylcarbonyloxy, alkoxycarbonyl, alkylsulphonyloxy, hydroximinoalkyl or alkoximinoalkyl which may each be straight-chain or branched and each have from 1 to 6 carbon atoms in the individual alkyl parts; phenyl, phenoxy, phenylthio, benzyloxy, benzylthio or phenylethyloxy, or by doubly linked alkylene having 3 or 4 carbon atoms or by doubly linked dioxyalkylene having 1 or 2 carbon atoms, with the two latter radicals themselves being able to be monosubstituted or polysubstituted, identically or differently, by halogen, straight-chain or branched alkyl having from 1 to 4 carbon atoms and/or straight-chain or branched halogenoalkyl having from 1 to 4 carbon atoms and from 1 to 9 identical or different halogen atoms.

$R^3$ preferably represents hydrogen, amino, or $R^3$ preferably represents straight-chain or branched alkyl having from 1 to 10 carbon atoms or straight-chain or branched alkoxy having from 1 to 6 carbon atoms, with the alkyl radicals or alkoxy radicals being able to be monosubstituted or polysubstituted, identically or differently, by halogen, nitro, amino, hydroxy, formyl, carboxy, carbamoyl;

and/or by alkoxy, alkylthio, alkylsulphinyl or alkylsulphonyl which may each be straight-chain or branched and each have from 1 to 6 carbon atoms;

and/or by straight-chain or branched alkenyl or straight-chain or branched alkenyloxy each having from 2 to 6 carbon atoms;

and/or by halogenoalkoxy, halogenoalkylthio, halogenoalkylsulphinyl or halogenoalkylsulphonyl which may each be straight-chain or branched and each have from 1 to 6 carbon atoms and from 1 to 13 identical or different halogen atoms;

and/or by alkylamino, dialkylamino, alkylcarbonyl, alkylcarbonyloxy, alkoxycarbonyl, alkylsulphonyloxy, hydroximinoalkyl or alkoximinoalkyl which may each be straight-chain or branched and each have from 1 to 6 carbon atoms in the individual alkyl parts;

or by doubly linked alkylene having from 1 to 6 carbon atoms or by doubly linked dioxyalkylene having from 1 to 4 carbon atoms, with the two latter radicals themselves being able to be monosubstituted or polysubstituted, identically or differently, by halogen, straight-chain or branched alkyl having from 1 to 4 carbon atoms and/or straight-chain or branched halogenoalkyl having from 1 to 4 carbon atoms and from 1 to 9 identical or different halogen atoms, or by phenyl, or $R^3$ preferably represents cycloalkyl having from 3 to 7 carbon atoms, with these radicals being able to be monosubstituted to tetrasubstituted, identically or differently, by halogen and/or alkyl having from 1 to 4 carbon atoms, or represents cycloalkenyl having from 3 to 7 carbon atoms, with these radicals being able to be monosubstituted to tetrasubstituted, identically or differently, by halogen and/or alkyl having from 1 to 4 carbon atoms, or represents saturated or unsaturated heterocyclyl having from 3 to 7 ring atoms of which in each case from 1 to 3 are identical or different hetero atoms such as oxygen, nitrogen or sulphur, with the radicals being able to be monosubstituted to trisubstituted, identically or differently, by halogen, alkyl having from 1 to 4 carbon atoms, alkoxy having from 1 to 4 carbon atoms and/or halogenoalkyl having from 1 to 4 carbon atoms and from 1 to 5 identical or different halogen atoms, or represents aryl having from 6 to 10 carbon atoms, with each of these radicals being able to be monosubstituted to pentasubstituted, identically or differently, by halogen, straight-chain or branched alkyl having from 1 to 4 carbon atoms, straight-chain or branched halogenoalkyl having from 1 to 4 carbon atoms and from 1 to 9 identical or different halogen atoms, straight-chain or branched alkoxy or alkylthio having from 1 to 4 carbon atoms, straight-chain or branched halogenoalkoxy or halogenoalkylthio having from 1 to 4 carbon atoms and from 1 to 9 identical or different halogen atoms, phenyl, phenoxy, phenylthio, benzyloxy, benzylthio or phenylethyloxy, or by doubly linked alkylene having 3 or 4 carbon atoms, or by doubly linked dioxyalkylene having 1 or 2 carbon atoms, with the two latter radicals themselves being able to be monosubstituted or polysubstituted, identically or differently, by halogen, straight-chain or branched alkyl having from 1 to 4 carbon atoms and/or straight-chain or branched halogenoalkyl having from 1 to 4 carbon atoms and from 1 to 9 identical or different halogen atoms.

n also particularly preferably represents the numbers 0, 1 or 2.

$R^1$ particularly preferably represents methyl, ethyl, n-propyl or isopropyl.

$R^2$ particularly preferably represents cyclohexyl, norbornyl or cyclohexenyl, with these radicals being able to be monosubstituted to tetrasubstituted, identically or differently, by fluorine, chlorine, methyl and/or ethyl, or represents furyl, pyridyl or thienyl, with these radicals being able to be monosubstituted to trisubstituted, identically or differently, by fluorine, chlorine, bromine, methyl, ethyl, n-propyl, i-propyl, n-butyl, i-butyl, s-butyl, t-butyl, methoxy, ethoxy, n-propoxy, i-propoxy, trifluoromethyl and/or trifluoroethyl, or represents phenyl or naphthyl, with each of these radicals being able to be monosubstituted to pentasubstituted, identically or differently, by fluorine, chlorine, bromine, nitro, amino, hydroxy, formyl, carboxy, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, methoxycarbonyl, ethoxycarbonyl, phenyl, phenoxy, phenylthio, benzyloxy, benzylthio or phenylethyloxy, or by in each case doubly linked trimethylene (propane-1,3-diyl), methylenedioxy or ethylenedioxy which may each be unsubstituted, monosubstituted or polysubstituted, identically or differently, by fluorine, chlorine, methyl, trifluoromethyl, ethyl, n- or i-propyl.

$R^3$ particularly preferably represents hydrogen, amino, methyl, ethyl, n- or i-propyl, n-, i-, s-butyl, pentyl, hexyl, heptyl, octyl, methoxy, ethoxy, hydroxymethyl, 1-hydroxy-1-ethyl, methoxymethyl, methoxyethyl, methoxypropyl, ethoxymethyl, ethoxyethyl, 2-carboxy-1-hydroxy-1-ethyl, 2-carboxy-1-ethyl, 3-carboxy-1-propyl or benzyl.

The optically active amides of the formula (II) are known and/or can be prepared by known methods (cf. DE-A 4332738 and Chimia 48, 570 (1994)).

Suitable diluents for carrying out the first stage of the process of the invention are all polar, aprotic, organic solvents. Preference is given to using nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoramide, sulphoxides such as dimethyl sulphoxide; sulphones such as sulpholane.

Suitable bases for carrying out the first stage of the process of the invention are all customary inorganic and organic acid binders having high basicity. Preference is given to using alkaline earth metal or alkali metal hydrides, hydroxides, amides or alkoxides, for example sodium hydride, sodium amide, sodium methoxide, sodium ethoxide, potassium tert-butoxide, sodium hydroxide or potassium hydroxide.

The reaction temperatures for carrying out the first stage of the process of the invention can be varied within a relatively wide range. Use is generally made of temperatures between 0° C. and 280° C., preferably between 20° C. and 250° C.

Both the first and second stages of the process of the invention are generally carried out under atmospheric pressure. However, it is also possible in each case to use increased or reduced pressure. Thus, the reactions can be carried out under pressures between 0.1 bar and 10 bar.

Furthermore, both the first and second stages of the process of the invention can be carried out under an inert gas atmosphere, preferably under nitrogen or argon.

In carrying out the first stage of the process of the invention, use is generally made of from 0.01 to 2 mol, preferably from 0.02 to 1 mol, of strong base per 1 mol of optically active amide of the formula (II). The work-up is carried out by customary methods. If the reaction is carried out in the absence of diluents, the procedure is generally to admix the reaction mixture with an organic solvent which is sparingly miscible with water, to wash the resulting mixture with water, then dry and evaporate it. If the reaction is carried out in the presence of diluents, the procedure is generally to evaporate the reaction mixture, to admix the residue with water, to extract with an organic solvent which is sparingly miscible with water and to dry and evaporate the combined organic phases.

For carrying out the second stage of the process of the invention according to variant (a), suitable bases are all customary strong inorganic and organic bases. Preference is given to those bases which have been specified as preferred in connection with the first stage of the process of the invention. Additional possibilities are acids such as dilute sulphuric acid and hydrochloric acid.

Suitable diluents for carrying out the second stage of the process of the invention according to variant (a) are all organic solvents customary for the saponification of amides. Preference is given to using alcohols such as methanol, ethanol, n-butanol and propanol, in addition dimethyl sulphoxide and also water, and mixtures of these solvents.

The reaction temperatures for carrying out the second stage of the process of the invention according to variant (a) can also be varied within a relatively wide range. Use is generally made of temperatures between 0° C. and 200° C., preferably between 20° C. and 150° C.

For carrying out the second stage of the process of the invention according to variant (a), use is generally made of from 0.1 to 5 mol, preferably from 1 to 3 mol, of base or acid per 1 mol of racemic amide of the formula (Ia). The work-up is carried out by customary methods. The procedure is generally to extract the reaction mixture, if desired after prior evaporation, with an organic solvent which is sparingly miscible with water, and to wash, dry and evaporate the combined organic phases.

For carrying out the second stage of the process of the invention according to variant (b), preferred hydroxides are sodium hydroxide, potassium hydroxide or calcium hydroxide.

The reaction temperatures for carrying out the second stage of the process of the invention according to variant (b) can also be varied within a relatively wide range. Use is generally made of temperatures between 40° C. and 220° C., preferably between 40° C. and 180° C.

For carrying out the second stage of the process of the invention according to variant (b), use is generally made of from 0.02 to 5 mol of alkali metal hydroxide or a corresponding amount of alkaline earth metal hydroxide per 1 mol of racemic amide of the formula (Ia). The work-up is carried out by customary methods. The procedure is generally to admix the reaction mixture with water, then extract it with an organic solvent which is sparingly miscible with water and to dry and evaporate the combined organic phases.

In a preferred embodiment, the procedure in carrying out the process of the invention is to generally use from 0.02 to 1.0 mol, preferably from 0.05 to 0.5 mol, of alkali metal hydroxide per 1 mol of optically active amide of the formula (II) and to heat the mixture to temperatures between 20° C. and 280° C., preferably between 50° C. and 250° C., so that a melt is formed. After racemization is complete (after from 0.5 to 36 hours), the resulting racemic amide of the formula (Ia) can be saponified by addition of from 20 to 2000 ml of water per mol of amide and, if desired, by addition of further alkali metal hydroxide or of alkaline earth metal hydroxide to give the racemic amine, by heating to temperatures between 20° C. and 100° C.

A further preferred embodiment of the process of the invention comprises using from 0.02 to 1.0 mol, preferably from 0.05 to 0.5 mol, of an alkali metal hydride, preferably sodium hydride, per 1 mol of optically active amide of the formula (II) and heating the mixture to temperatures between 20° C. and 280° C., preferably between 50° C. and 250° C., so that a melt is formed. If desired, this can be followed by saponification of the amide.

In a further preferred embodiment, the procedure for the process of the present invention is to use from 0.02 to 1.0 mol, preferably from 0.05 to 0.5 mol, of an alkali metal or alkaline earth metal alkoxide, preferably potassium tert-butoxide per 1 mol of optically active amide of the formula (II) and to work in the presence of a polar, aprotic, organic solvent. As solvents, preference is here given to using nitriles such as acetonitrile, propionitrile, n- or i-butyronitrile or benzonitrile; also amides such as N,N-dimethylformamide, N,N-dimethylacetamide, N-methylformanilide, N-methylpyrrolidone or hexamethylphosphoramide; in addition sulphoxides such as dimethyl sulphoxide; and also sulphones such as sulpholane, optionally also in admixture with alcohols such as tert-butanol.

This can be followed by saponification of the amide.

In another preferred embodiment, the procedure for the process of the invention is to generally use from 0.02 to 1.0 mol, preferably from 0.05 to 0.5 mol, of a metal alkoxide, preferably an alkali metal, alkaline earth metal or earth metal alkoxide, in particular potassium tert-butoxide, per 1 mol of optically active amide of the formula (II) and to heat the mixture to temperatures between 40° C. and 220° C., so that a melt is formed. If the amide of the formula (II) is a compound in which $R^3$ is hydrogen, then the corresponding racemic amine can be obtained directly after the racemization step by addition of from 0.02 to 5 mol of an alkali metal or alkaline earth metal hydroxide, such as sodium hydroxide, potassium hydroxide or calcium hydroxide, per mol of amide and again heating to temperatures between 40° C. and 220° C. (from 0.5 to 24 hours).

In a further preferred embodiment of the process of the invention, the procedure is to use generally from 0.02 to 1 mol, preferably from 0.05 to 0.5 mol, of an alkali metal, alkaline earth metal or earth metal hydroxide, in particular potassium hydroxide, per 1 mol of optically active amide of the formula (II) and to work in the presence of a polar, aprotic, organic solvent. As solvents, preference is here given to using nitriles such as acetonitrile, propionitrile, n- or i-butyronitrile or benzonitrile; also amides such as N,N-dimethylformamide, N,N-dimethylacetamide, N-methylformanilide, N-methylpyrrolidone or hexamethylphosphoramide; in addition sulphoxides such as dimethyl sulphoxide; and also sulphones such as sulpholane, optionally in admixture with alcohols such as tert-butanol.

Saponification of the amide can follow.

The racemic amides and amines obtainable by the process of the invention can be used directly or after prior resolution of the racemate as intermediates for further syntheses. Particularly (R)-amines of the formula (I) are valuable intermediates for preparing pharmaceuticals or active compounds having insecticidal, fungicidal or herbicidal properties (cf. EP-A 0 519 211, EP-A 0 453 137, EP-A 0 283 879, EP-A 0 264 217 and EP-A 0 341 475). Thus, for example, the fungicidally active compound of the formula

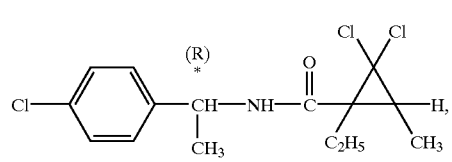

(III)

is obtained by reacting the (R)-1-(4-chloro-phenyl)-ethylamine of the formula

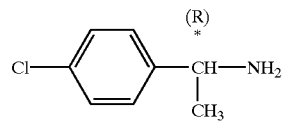

(IV)

with 2,2-dichloro-1-ethyl-3-methyl-1-cyclopropanecarboxylic chloride of the formula

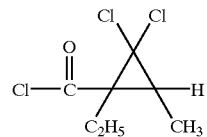

(V)

in the presence of an acid binder and in the presence of an inert organic diluent.

The procedure for the process of the invention is illustrated by the following examples.

Preparative Examples

EXAMPLE 1

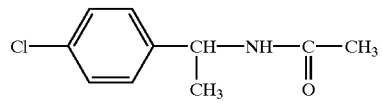

(I-1)

4 g (0.020 mol) in each case of (S)-N-[1-(4-chlorophenyl)-ethyl]-acetamide are heated at from 130 to 140° C. with the amounts of potassium hydroxide indicated in Tables 1 to 3 for the time indicated in each case, so that a melt is formed. The course of the reaction is here monitored by taking samples. The measure used for the degree of racemization is the ee value, which indicates the enantiomeric excess and is calculated as follows:

$$ee = \frac{(R-S)}{(R+S)} \times 100\%.$$

R and S are here the concentrations of the individual enantiomers of the amide formed.

After the reaction is complete, the melt is allowed to cool, 100 ml in each case of methyl tert-butyl ether are added, the mixture formed is washed with water, the organic phase is dried over sodium sulphate and evaporated under reduced pressure. This gives racemic N-[1-(4-chloro-phenyl)-ethyl]-acetamide in yields between 95 and 100%.

TABLE 1

| Amount of potassium hydroxide used: 20 mol % | | | | | | | | |
|---|---|---|---|---|---|---|---|---|
| ee Value (%) (S)-N-[1-(4-chlorophenyl)-ethyl]-acetamide | 63.3 | 39.9 | 23.9 | 15.4 | 9.04 | 5.65 | 3.86 | 1.28 |
| Reaction time (hours) | 0 | 0.5 | 1 | 1.5 | 2 | 2.5 | 3 | 4 |

TABLE 2

| Amount of potassium hydroxide used: 10 mol % | | | | | | | | |
| --- | --- | --- | --- | --- | --- | --- | --- | --- |
| ee Value (%) (S)-N-[1-(4-chlorophenyl)-ethyl]-acetamide | 63.5 | 49.8 | 37.8 | 30.5 | 20.2 | 14.8 | 7.5 | 4 |
| Reaction time (hours) | 0 | 0.5 | 1 | 2 | 3 | 4 | 6 | 12 |

TABLE 3

| Amount of potassium hydroxide used: 50 mol % | | | | | | | | |
| --- | --- | --- | --- | --- | --- | --- | --- | --- |
| ee Value (%) (S)-N-[1-(4-chlorophenyl)ethyl]-acetamide | 63 | 36.3 | 22.1 | 14.2 | 10 | 4.8 | 2.9 | 2 |
| Reaction time (hours) | 0 | 0.5 | 1 | 1.5 | 2 | 3 | 4 | 6 |

EXAMPLE 2

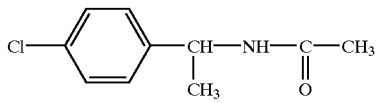
(I-1)

A mixture of 9.87 g (0.05 mol) of (S)-N-[1-(4-chlorophenyl)-ethyl]acetamide having an ee value of 64% and 0.15 g (0.005 mol) of sodium hydroxide is heated at from 140 to 150° C. for 20 hours under argon. The melt is then allowed to cool, 200 ml of water are added, the mixture is extracted with methyl tert-butyl ether, the combined organic phases are dried over sodium sulphate and evaporated under reduced pressure. This gives 9.45 g of N-[1-(4-chlorophenyl)-ethyl]-acetamide having an ee value of 2.5%. The yield of racemic product can thus be calculated as 95.6% of theory.

EXAMPLE 3

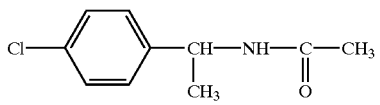
(I-1)

A mixture of 3.95 g (0.02 mol) of (S)-N-[1-(4-chlorophenyl)-ethyl]-acetamide having an ee value of 64%, 0.45 g (0.004 mol) of potassium tert-butoxide and 24 ml of dimethyl sulphoxide is heated at 90° C. for 24 hours. The reaction mixture is then evaporated under reduced pressure and the residue is admixed with 50 ml of water. The mixture formed is extracted with methyl tert-butyl ether, the combined organic phases are dried over sodium sulphate and evaporated under reduced pressure. This gives 3.45 g of N-[1-(4-chloro-phenyl)-ethyl]-acetamide having an ee value of 12.5%. The yield of racemic product can thus be calculated as 94% of theory.

EXAMPLE 4

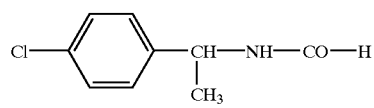
(I-2)

A mixture of 2.76 g (0.015 mol) of (S)-N-[1-(4-chlorophenyl)-ethyl]-formamide having an ee value of 64%, 0.37 g (3.3 mol) of potassium tert-butoxide and 15 ml of dimethyl sulphoxide is heated at 90° C. for 30 hours. The reaction mixture is then evaporated under reduced pressure and the residue is admixed with 50 ml of water. The mixture formed is extracted with methyl tert-butyl ether, the combined organic phases are dried over sodium sulphate and evaporated under reduced pressure. This gives 2 g of N-[1-(4-chloro-phenyl)-ethyl]-formamide having an ee value of 3.9%. The yield of racemic product can thus be calculated as 74% of theory.

EXAMPLE 5

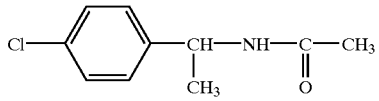
(I-1)

A mixture of 3.95 g (0.02 mol) of (S)-N-[1-(4-chlorophenyl)-ethyl]-acetamide having an ee value of 64% and 0.45 g (0.004 mol) of potassium tert-butoxide is heated at 150° C. for 24 hours. The melt is then allowed to cool, 50 ml of methyl tert-butyl ether are added, the mixture is washed with water, the organic phase is dried over sodium sulphate and evaporated under reduced pressure. This gives 3.67 g of N-[1-(4-chloro-phenyl)-ethyl]-acetamide having an ee value of 0%. The yield of racemic product can thus be calculated as 90.3% of theory.

EXAMPLE 6

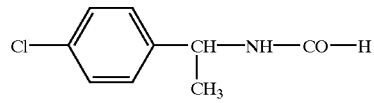
(I-2)

A mixture of 2.76 g (0.015 mol) of (S)-N-[1-(4-chlorophenyl)-ethyl]-formamide having an ee value of 64% and 0.336 g (0.0029 mol) of potassium tert-butoxide is heated at 150° C. for 20 hours. The melt is then allowed to cool, 50 ml of methyl tert-butyl ether are added, the mixture is washed with water, the organic phase is dried over sodium sulphate and evaporated under reduced pressure. This gives 2.56 g of N-[1-(4-chloro-phenyl)-ethyl]-formamide having an ee value of 2.6%. The yield of racemic product can thus be calculated as 93.3% of theory.

EXAMPLE 7

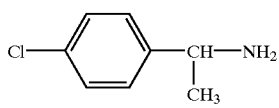
(I-3)

A mixture of 9.5 g (0.0517 mol) of (S)-N-[1-(4-chloro-phenyl)-ethyl]-formamide having an ee value of 64% and 1.55 g (0.0138 mol) of potassium tert-butoxide is heated at 150° C. for 24 hours. The mixture is then cooled, admixed with 3.75 g (0.056 mol) of powdered potassium hydroxide and heated at 150° C. for 20 hours. After the melt has cooled, 100 ml of water are added, the mixture is extracted with dichloromethane, the combined organic phases are dried over sodium sulphate and evaporated under reduced pressure. This gives 7.3 g of 1-(4-chlorophenyl)-ethyl-amine having an ee value of 0%. The yield of racemic product can thus be calculated as 91.6% of theory.

EXAMPLE 8

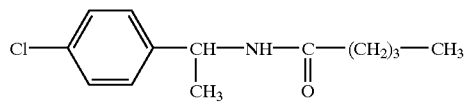
(I-4)

A mixture of 2.4 g (0.01 mol) of (S)-N-[1-(4-chloro-phenyl)-ethyl]-valeramide ($[\alpha]_D^{20}=-105.1°$ c=1 in methanol) and 1.12 g (0.01 mol) of potassium tert-butoxide is heated at 120° C. for 30 hours. After the melt has cooled, 50 ml of dichloromethane are added, the mixture is washed with water, the organic phase is dried over sodium sulphate and evaporated under reduced pressure.

This gives 1.93 g of N-[1-(4-chloro-phenyl)-ethyl]-valeramide ($[\alpha]_D^{20}=\pm0°$ c=1.01 in methanol). The yield of racemic product can thus be calculated as 80.29% of theory.

EXAMPLE 9

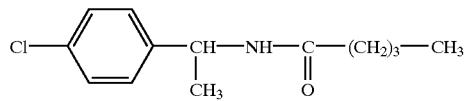
(I-4)

A mixture of 2.4 g (0.01 mol) of (S)-N-[1-(4-chloro-phenyl)-ethyl]-valeramide ($[\alpha]_D^{20}=-105.1°$ c=1 in methanol), 0.56 g (0.005 mol) of potassium tert-butoxide and 20 ml of dimethyl sulphoxide is heated at 100° C. for 30 hours. The reaction mixture is then evaporated under reduced pressure and the residue is admixed with 50 ml of dichloromethane. The mixture formed is washed three times with 20 ml each time of water, dried over sodium sulphate and evaporated under reduced pressure.

This gives 2.05 g of N-[1-(4-chloro-phenyl)-ethyl]-valeramide ($[\alpha]_D^{20}=-100°$ c=1.1 in methanol). The yield of racemic product can thus be calculated as 85.8% of theory.

EXAMPLE 10

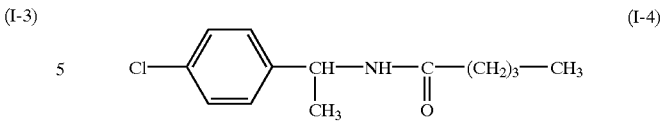
(I-4)

A mixture of 2.4 g (0.01 mol) of (S)-N-[1-(4-chloro-phenyl)-ethyl]-valeramide ($[\alpha]_D^{20}=-105.1°$ c=1 in methanol), 0.27 g (0.004 mol) of potassium hydroxide and 15 ml of dimethyl sulphoxide is heated at 100° C. for 32 hours. The reaction mixture is then evaporated under reduced pressure and the residue is admixed with 50 ml of dichloromethane. The mixture formed is washed three times with 20 ml each time of water, dried over sodium sulphate and evaporated under reduced pressure.

This gives 1.96 g of N-[1-(4-chloro-phenyl)-ethyl]-valeramide ($[\alpha]_D^{20}=\pm0°$ c=1.141 in methanol). The yield of racemic product can thus be calculated as 81.7% of theory.

EXAMPLE 11

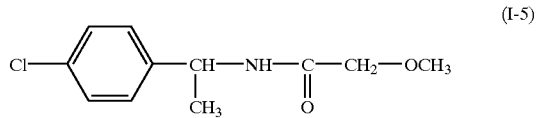
(I-5)

A mixture of 2.3 g (0.01 mol) of (S)-N-[1-(4-chloro-phenyl)-ethyl]-2-methoxy-acetamide ($[\alpha]_D^{20}=-78.9°$ c=1 in methanol), 0.33 g (0.005 mol) of potassium hydroxide and 15 ml of dimethyl sulphoxide is heated at 100° C. for 32 hours. It is then worked up in the manner described in Example 10. This gives 1.96 g of N-[1-(4-chloro-phenyl)-ethyl]-2-methoxy-acetamide ($[\alpha]_D^{20}=\pm0°$ c=1.14 in methanol). The yield of racemic product can thus be calculated as 85.2% of theory.

EXAMPLE 12

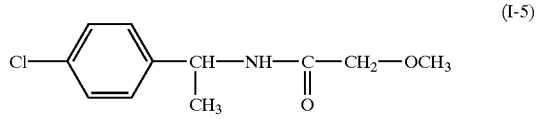
(I-5)

A mixture of 2.3 g (0.01 mol) of (S)-N-[1-(4-chloro-phenyl)-ethyl]-2-methoxy-acetamide ($[\alpha]_D^{20}=-78.90°$ c=1 in methanol), 0.56 g (0.005 mol) of potassium tert-butoxide and 15 ml of dimethyl sulphoxide is heated at 100° C. for 32 hours. It is then worked up in the manner described in Example 9. This gives 1.95 g of N-[1-(4-chloro-phenyl)-ethyl]-2-methoxy-acetamide ($[\alpha]_D^{20}=-2.9°$ c=1.01 in methanol). The yield of racemic product can thus be calculated as 85.2% of theory.

It is understood that the specification and examples are illustrative but not limitative of the present invention and that other embodiments within the spirit and scope of the invention will suggest themselves to those skilled in the art.

What is claimed is:

1. A process for preparing a racemic amino acid derivative of the formula:

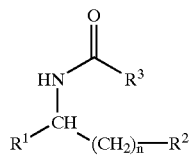

in which n represents the numbers 0, 1 or 2, $R^1$ represents methyl, ethyl, n-propyl or isopropyl;

$R^2$ represents cyclohexyl, norbornyl or cyclohexenyl, or represents monosubstituted to tetrasubstituted cyclohexyl, norbornyl or cyclohexenyl, the substituents being identical or different and being, in each case, selected from the group consisting of fluorine, chlorine, methyl and ethyl, or represents furyl, pyridyl or thienyl, or represents monosubstituted to trisubstituted furyl, pyridyl or thienyl, the substituents being identical or different and being, in each case, selected from the group consisting of fluorine, chlorine, bromine, methyl, ethyl, n-propyl, i-propyl, n-butyl, i-butyl, s-butyl, t-butyl, methoxy, ethoxy, n-propoxy, i-propoxy, trifluoromethyl and trifluoroethyl;

or represents phenyl, naphthyl or monosubstituted to pentasubstituted phenyl or naphthyl, the substituents being identical or different and being, in each case, selected from the group consisting of fluorine, chlorine, bromine, nitro, amino hydroxy, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsuphinyl, ethylsulphinyl, methylsulphonyl- or ethylsulphonyl, trifluoromethyl, trifluoroethyl, difluoromethoxy, trifluoromethoxy, difluorochloromethoxy, trifluoroethoxy, difluorochloromethylthio, difluoromethylthio, trifluoromethylthio, trifluoromethylsulphinyl or trifluoromethylsulphonyl, methylamino, ethylamino, n- or i-propylamino, dimethylamino, diethylamino, methoxycarbonyl, ethoxycarbonyl, phenyl, phenyloxy, phenylthio, benzyloxy, benzylthio or phenylethyloxy, or by in each case doubly linked trimethylene (propane-1,3-diyl), methylenedioxy or ethylenedioxy which may each be unsubstituted, mono-substituted or polysubstituted, identically or differently, by fluorine, chlorine, methyl, trifluoromethyl, ethyl, n- or i-propyl, and $R^3$ represents hydrogen, amino, methyl, ethyl, n- or i-propyl, n-, i-, s-butyl, pentyl, hexyl, heptyl, octyl, methoxy, ethoxy, hydroxymethyl, 1-hydroxy-1-ethyl, methoxymethyl, methoxyethyl, methoxypropyl, ethoxymethyl, ethoxyethyl, 2-carboxy-1-hydroxy-1-ethyl, 2-carboxy-1-ethyl, 3-carboxy-1-propyl or benzyl;

which process comprises reacting an optically active amide of the formula

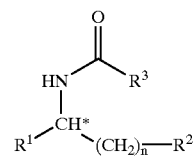

in which $R^1$, $R^2$, $R^3$ and n are as defined above, with a strong base, optionally in the presence of an organic diluent.

2. A process according to claim 1, wherein (S)-N-[1-(4-chloro-phenyl)-ethyl]-acetamide of the formula

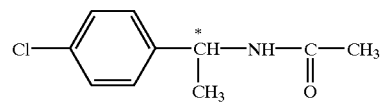

is employed as an optically active amide.

3. A process according to claim 1, wherein (S)-N-[1-(4-chloro-phenyl)-ethyl]-formamide of the formula

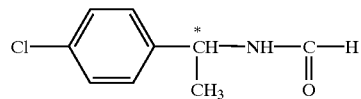

is employed as an optically active amide.

4. A process according to claim 1, wherein (S)-N-[1-(4-chloro-phenyl)-ethyl]valeramide of the formula

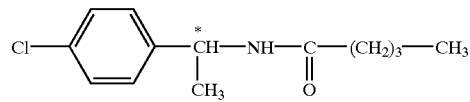

is employed as an optically active amide.

5. A process according to claim 1, wherein (S)-N-[1-(4-chloro-phenyl)-ethyl]-2-methoxy-acetamide of the formula

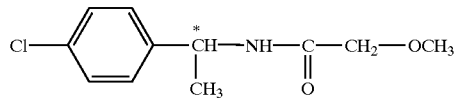

is employed as an optically active amide.

6. A process according to claim 1, wherein (S)-N-[1-(4-chloro-phenyl)-ethyl]-benzylamide of the formula

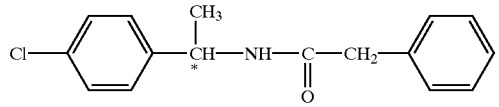

is employed as an optically active amide.

7. A process according to claim 1, wherein the optically active amide is selected from the group consisting of (S)-N-[1-(4-chloro-phenyl)-ethyl]-acetamide

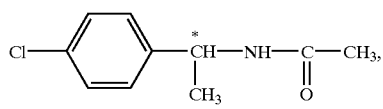

(S)-N-[1-(4-chloro-phenyl)-ethyl]-formamide

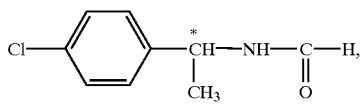

(S)-N-[1-(4-chloro-phenyl)-ethyl]-valeramide

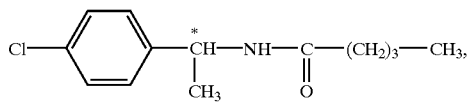

(S)-N-[1-(4-chloro-phenyl)-ethyl]-2-methoxy-acetamide

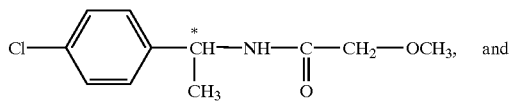

(S)-N-[1-(4-chloro-phenyl)-ethyl]-benzylamide

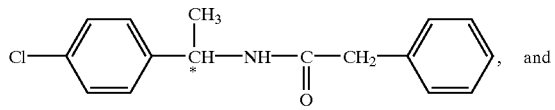

the reaction is carried out at a temperature between about 0° C. and 280° C. using from about 0.01 to 2 mol of a strong base per mol of optically active amide.

8. The process according to claim 1, wherein the diluent of the process is a nitrile, an amide, a sulphoxide or a sulphone.

9. The process according to claim 5, wherein the nitrile is acetonitrile, propionitrile, n- or i-butyronitrile or benzonitrile;

the amide is N, N-dimethylformamide, N,N-dimethylacetamide;

N-methylformanilide, N-methylpyrrolidone or hexamethylphosphoramide;

the sulphoxide is dimethyl sulphoxide; and the sulphone is sulpholane.

10. The process according to claim 1, wherein the base of the process is an alkaline earth metal or an alkali metal hydride, hydroxide, amide or alkoxide.

11. The process according to claim 10, wherein the base is sodium hydride, sodium amide, sodium methoxide, sodium ethoxide, potassium tert-butoxide, sodium hydroxide or potassium hydroxide.

12. A process for preparing a racemic amino derivative of the formula:

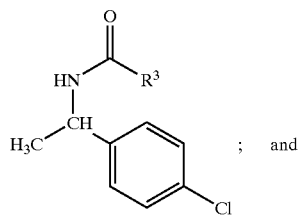

in which $R^3$ represents hydrogen, methyl, n-butyl or methyoxymethyl, which process comprises reacting an optically active amide of the formula

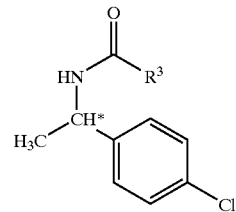

in which $R^3$ has the above-mentioned meaning, with a strong base in the presence of an organic diluent of a temperature between 0° C. and 280° C.

13. A process for preparing a racemic amino derivative of the formula:

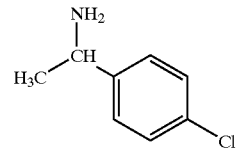

which process comprises reacting an optically active amide of the formula:

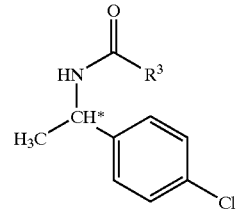

in which $R^3$ represents hydrogen, methyl, n-butyl or methyoxymethyl, with a strong base in the presence of an organic diluent of a temperature between 0° C. and 280° C., and
reacting the resulting amide of the formula:

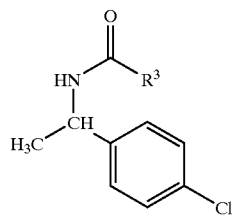

in which

R³ has the above-mentioned meaning, either a) with water in the presence of a base or an acid and in the presence of an organic diluent at a temperature between 0° C. and 200° C., or b) if the compound of the above-mentioned formula is an amide in which R³ is hydrogen, with an alkali metal hydroxide or an alkaline earth metal hydroxide at a temperature between 0° C. and 200° C.

* * * * *